(12) United States Patent
Klebba

(10) Patent No.: US 8,695,413 B2
(45) Date of Patent: Apr. 15, 2014

(54) METHOD FOR EVALUATING THE STICKINESS OF AN OUTER SURFACE ON AN ABSORBENT ARTICLE

(75) Inventor: Christian Klebba, Eschborn (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/479,642

(22) Filed: May 24, 2012

(65) Prior Publication Data

US 2012/0304782 A1 Dec. 6, 2012

Related U.S. Application Data

(60) Provisional application No. 61/491,289, filed on May 30, 2011.

(51) Int. Cl.
*G01B 21/08* (2006.01)

(52) U.S. Cl.
USPC .......................................... 73/150 A; 73/862

(58) Field of Classification Search
USPC ........... 73/150 A, 150 R, 159, 826; 33/150 A
See application file for complete search history.

(56) References Cited

U.S. PATENT DOCUMENTS

| 4,798,646 | A | * | 1/1989 | Sumi ............................ 156/364 |
| 6,004,308 | A | | 12/1999 | Haddock |
| 6,623,464 | B2 | | 9/2003 | Bewick-Sonntag et al. |
| 6,815,653 | B2 | * | 11/2004 | Tsay et al. .................... 250/206 |
| 7,312,865 | B2 | * | 12/2007 | Chen .......................... 356/237.2 |
| 7,402,723 | B2 | | 7/2008 | Stone et al. |
| 7,521,588 | B2 | | 4/2009 | Stone et al. |
| 7,628,066 | B2 | * | 12/2009 | Deng et al. .................. 73/150 A |
| 8,021,564 | B2 | * | 9/2011 | Sakuragi et al. ................ 216/59 |
| 2003/0149387 | A1 | | 8/2003 | Barakat et al. |
| 2007/0100313 | A1 | | 5/2007 | Luizzi |
| 2011/0303027 | A1 | * | 12/2011 | Shirazi et al. ................ 73/866.5 |

FOREIGN PATENT DOCUMENTS

| EP | 1 779 828 A1 | 5/2007 |
| JP | 2010-018539 | 1/2010 |
| JP | 2011-015707 | 1/2011 |

OTHER PUBLICATIONS

International Search Report, PCT/US2012/039938, mailed Aug. 28, 2012, 8 pages.

* cited by examiner

*Primary Examiner* — Max Noori
(74) *Attorney, Agent, or Firm* — Andrés E. Velarde; Brian M. Bolam

(57) ABSTRACT

A method of evaluating the stickiness of an outer surface of an absorbent article is disclosed. The method includes providing an absorbent article on a stationary horizontal surface, wherein the absorbent article has an outer surface facing away from the stationary horizontal surface. The method further includes affixing an adhesive substrate to the outer surface of the absorbent article, grasping an end portion of the adhesive substrate, and lifting the end portion of the adhesive substrate in a direction away from the stationary horizontal surface.

19 Claims, 4 Drawing Sheets

METHOD FOR EVALUATING THE STICKINESS OF AN OUTER SURFACE ON AN ABSORBENT ARTICLE

CROSS REFERENCE TO RELATED APPLICATION

This application claims the benefit of U.S. Provisional Application No. 61/491,289 filed on May 30, 2011.

FIELD OF THE INVENTION

The present invention relates to a method for evaluating the stickiness of an outer surface of an absorbent article, in particular evaluating the stickiness of a topsheet of a feminine hygiene article.

BACKGROUND OF THE INVENTION

Absorbent articles, such as feminine hygiene articles, are important for consumers. In particular, comfort during wearing of the absorbent article is important. Many factors can impact whether a consumer finds an absorbent article comfortable to wear, such as stickiness, rewet performance, softness, and the like. Many absorbent articles today are made with topsheet materials constructed of synthetic plastic materials, such as thermoplastic film materials and synthetic fibrous nonwoven materials. These topsheet materials will typically have various tradeoffs with respect to the various aspects of comfort.

Stickiness can be an important factor with regard to the overall comfort associated with wearing an absorbent article, but stickiness can often be difficult to evaluate. With regard to stickiness of an absorbent article during wear, it can be difficult to predict what types of topsheet materials are likely to be less sticky during wear than other types of topsheet materials. It is therefore desired to develop a method for evaluating the stickiness of an outer surface of an absorbent article that provides an indication as to the stickiness of the absorbent article during wear.

SUMMARY OF THE INVENTION

A method of evaluating the stickiness of an outer surface of an absorbent article comprises the steps of: (i) providing an absorbent article on a stationary horizontal surface, the absorbent article having an outer surface facing away from the stationary horizontal surface, (ii) affixing an adhesive substrate to the outer surface of the absorbent article, (iii) grasping an end portion of the adhesive substrate, and (iv) lifting the end portion of the adhesive substrate in a direction away from the stationary horizontal surface. If the adhesive substrate partially or fully detaches from the outer surface of the absorbent article, this provides an indication that the outer surface will tend to feel less sticky to a wearer of the article during use, as compared to an absorbent article wherein the adhesive substrate does not detach or only minimally detaches from the outer surface of the absorbent article upon lifting the end portion of the adhesive substrate away from the stationary surface. The present invention therefore provides an efficient qualitative method to evaluate the stickiness of an outer surface, especially the topsheet, of an absorbent article.

DETAILED DESCRIPTION OF THE INVENTION

Figure 1:
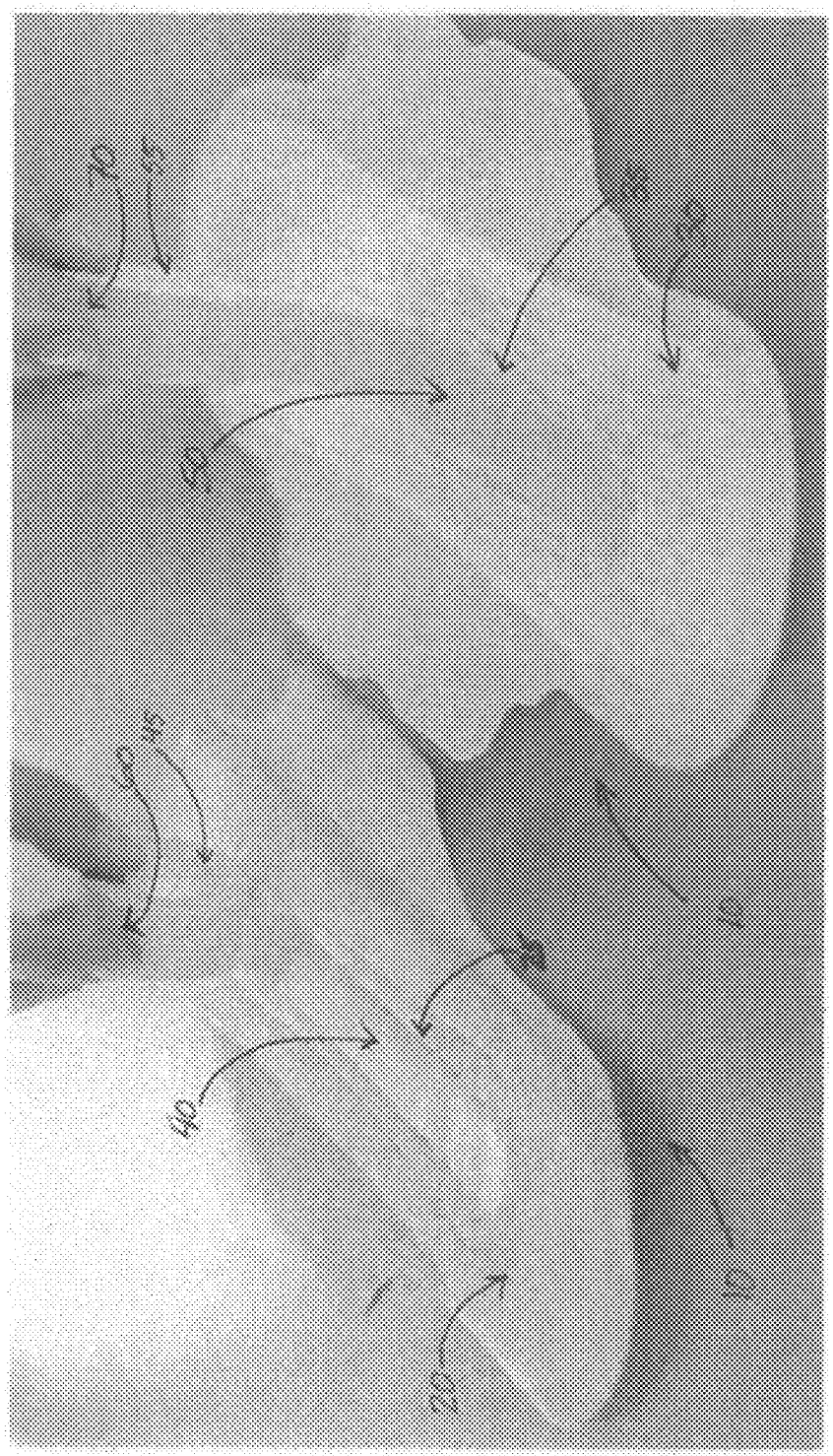
FIG. 1 is a perspective view of an embodiment of a method of the present invention for evaluating the comparative stickiness of two absorbent articles.

As used herein, the term "absorbent article" refers to devices that absorb and contain body exudates, primarily menses and/or urine. The term "disposable" is used herein to describe absorbent articles which are not intended to be laundered or otherwise restored or reused as an absorbent article after a single use. Examples of absorbent articles include feminine hygiene garments such as sanitary napkins, pantiliners, interlabial devices, hemorrhoid pads, wipes, tampons, and the like.

Disposable absorbent articles and components thereof, including the topsheet, backsheet, absorbent core, and any individual layers of these components, have a body surface and a garment surface. As used herein, "body surface" means that surface of the article or component which is intended to be worn toward or adjacent to the body of the wearer, while the "garment surface" is on the opposite side and is intended to be worn toward or placed adjacent to the wearer's undergarments when the disposable absorbent article is worn.

The method of the present invention for evaluating the stickiness of an absorbent article includes providing the absorbent article on a stationary horizontal surface, such as a table or desk. The surface does not have to be absolutely stationary or absolutely horizontal, as long as the absorbent article itself can sit stationary on the surface. An outer surface of the absorbent article, such as a top outer surface comprising a topsheet of the absorbent article, faces away from the stationary horizontal surface. Absorbent articles suitable for the methods of the present invention are described hereinafter.

The method further includes affixing an adhesive substrate to the outer surface of the absorbent article. Adhesive substrates suitable for the methods of the present invention are described hereinafter. The adhesive substrate is affixed to the outer surface by placing and/or pressing an adhesive side of the adhesive substrate against the outer surface of the absorbent article.

The method further includes grasping an end portion of the adhesive substrate. The end portion of the adhesive substrate can be grasped by hand or by a machine. The method of the present invention is intended to provide a qualitative evaluation of stickiness of the outer surface of an absorbent article, especially in comparison to another absorbent article, so the adhesive substrate is preferably grasped by hand. However, if the end portion is grasped by a machine, for example an INSTRON peel testing machine, then quantitative measurements relative to the peel strength between the outer surface of the absorbent article and the adhesive substrate can be possible to further evaluate the stickiness of the outer surface of the absorbent article.

The method further includes lifting the end portion of the adhesive substrate in a direction away from the stationary horizontal surface, preferably in a direction generally perpendicular to the stationary horizontal surface. Depending upon the stickiness of the outer surface of the absorbent article being evaluated, lifting of the end portion of the adhesive tape may also result in lifting the absorbent article itself away from the stationary horizontal surface. If the absorbent article has an outer surface that has reduced stickiness, the adhesive substrate will detach from the outer surface of the absorbent article upon lifting the end portion of the adhesive substrate away from the stationary horizontal surface.

The method can optionally further include providing more than one absorbent article, affixing an adhesive substrate to the outer surface of each absorbent article, grasping the end portions of each adhesive substrate and lifting the end portions in a direction away from the stationary horizontal surface, preferably simultaneously (i.e. at the same time). The adhesive substrate affixed to the outer surface of each absorbent article is preferably the same. This aspect of a method of the present invention facilitates a more direct comparison of the stickiness of the outer surfaces of the absorbent articles.

Since the method of the present invention provides a qualitative evaluation of stickiness, it is beneficial to tested two or more absorbent articles side-by-side with the same adhesive substrate to evaluate relative stickiness. When testing two or more absorbent articles to evaluate relative qualitative stickiness in a comparative fashion, the absorbent articles utilized in a method of the present invention will preferably have similar weight.

Figure 3:
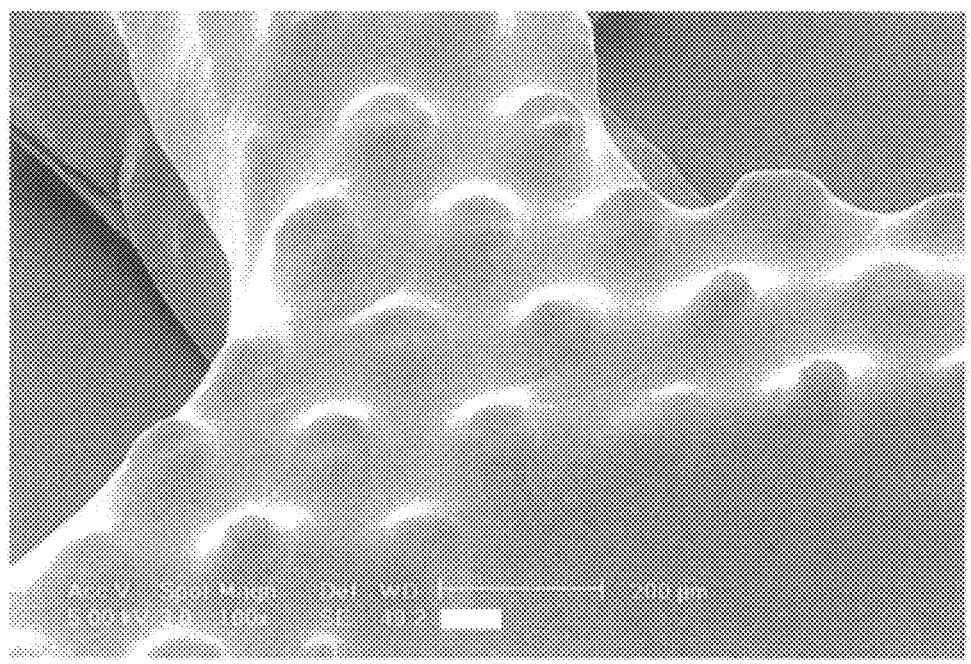
FIG. 3 is a photomicrograph of a topsheet of an absorbent article utilized in a method of the present invention.

FIG. 1 illustrates a method of evaluating the stickiness of a first absorbent article 20 and a second absorbent article 30. The absorbent articles 20, 30 are sanitary napkins. Each absorbent article 20, 30 is placed on a stationary horizontal surface 10, which is a table top. The first absorbent article 20 comprises a topsheet which is a nonwoven topsheet. The second absorbent article 30 comprises a preferred topsheet as described hereinafter, which is a thermoplastic film comprising a plurality of discrete extended elements, the discrete extended elements having a generally columnar shape and an average aspect ratio of about 0.6 (and as shown in FIG. 3). A first roll of adhesive tape 45 and a second roll of adhesive tape 55 are provided, each roll comprising the same adhesive tape. The adhesive tape 40 of the first roll of adhesive tape 45 is unrolled and affixed to the outer surface 25 of the first absorbent article 20. The adhesive tape 50 of the second roll of adhesive tape 55 is unrolled and affixed to the outer surface 35 of the second absorbent article 30. The amount of adhesive tape applied to each outer surface is approximately 1.7 cm wide by ⅔ the length of each absorbent article. The end portion 60 of the adhesive tape 40 affixed to the first absorbent article 20 and the end portion 70 of the adhesive tape 50 affixed to the second absorbent article 30 are grasped by hand. The end portions 60, 70 are lifted at the same time in a direction generally perpendicular to the stationary horizontal surface 10. The adhesive tape 50 affixed to the outer surface 35 of the second absorbent article 30 fully detaches from the outer surface 35, whereas the adhesive tape 40 affixed to the outer surface 25 of the first absorbent article 20 only minimally detaches from the outer surface 25. This comparative evaluation indicates that the outer surface 35 of the second absorbent article 30 has reduced stickiness as compared to the outer surface 25 of the first absorbent article 20.

Absorbent Article

In general, the absorbent article provided for the method of the present invention will have an outer surface, in particular a top outer surface and a bottom outer surface. The top outer surface will typically comprise a topsheet material and the bottom outer surface will typically comprise a backsheet material. An absorbent core material will typically be disposed in between the topsheet material and the backsheet material. Therefore, an absorbent article can comprise a topsheet material, a backsheet material, and an absorbent core material disposed therebetween.

The backsheet and the topsheet typically comprise the outer surface(s) of the absorbent article and are positioned adjacent the garment surface and the body surface, respectively, of the absorbent core. The absorbent core can be joined with the topsheet, the backsheet, or both in any manner as is known by attachment means such as those well known in the art. However, embodiments of the present invention are envisioned wherein portions of the entire absorbent core are unattached to either the topsheet, the backsheet, or both.

Figure 2:
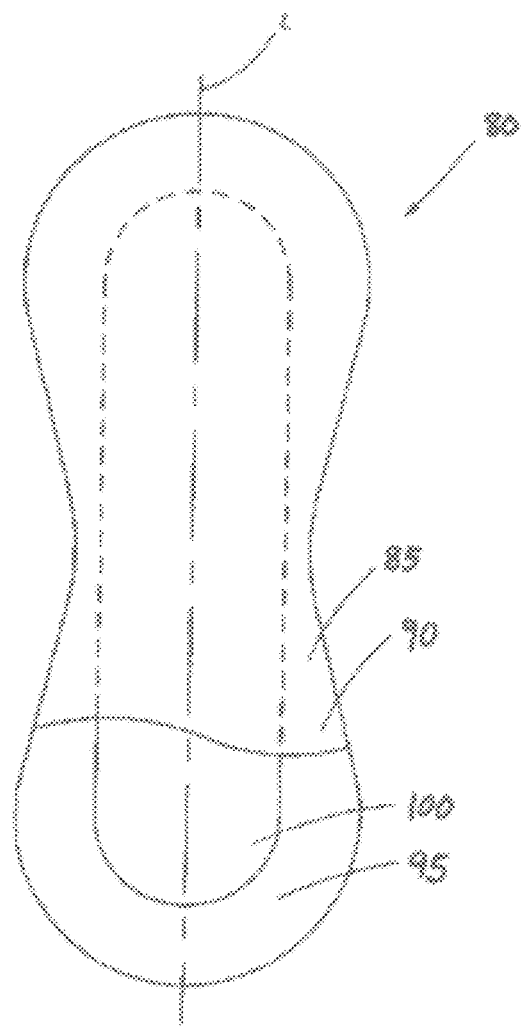
FIG. 2 is a top view of an absorbent article comprising a topsheet, backsheet, and an absorbent core.

FIG. 2 shows an absorbent article 80, that can be a sanitary napkin or pantiliner, having a body facing surface 85 comprising a topsheet 90, a liquid impervious backsheet 95 joined to the topsheet 90, an absorbent core 100. The absorbent article 80 has a longitudinal axis L and may also be provided with additional features commonly found in napkins, including "wings" or "flaps" (not shown) as is known in the art and/or a fluid acquisition layer to promote fluid transport to the absorbent core 100. Likewise, the topsheet of the absorbent article can have various optional characteristics, as is known in the art. For example, the topsheet 90 can have channels embossed therein to direct fluid flow, and can have apertures therethrough to aid in fluid acquisition.

The topsheet is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

To provide an absorbent article having an outer surface that exhibits reduced stickiness, the absorbent article preferably comprises a topsheet comprising a plurality of discrete extended elements. Such preferred topsheet materials are described in detail in, e.g., U.S. Pat. Nos. 7,402,723 or 7,521,588. The discrete extended elements of such a topsheet will typically have a generally columnar shape and an aspect ratio of at least about 0.2.

A photomicrograph of a preferred topsheet is shown in FIG. 3.

Figure 4:
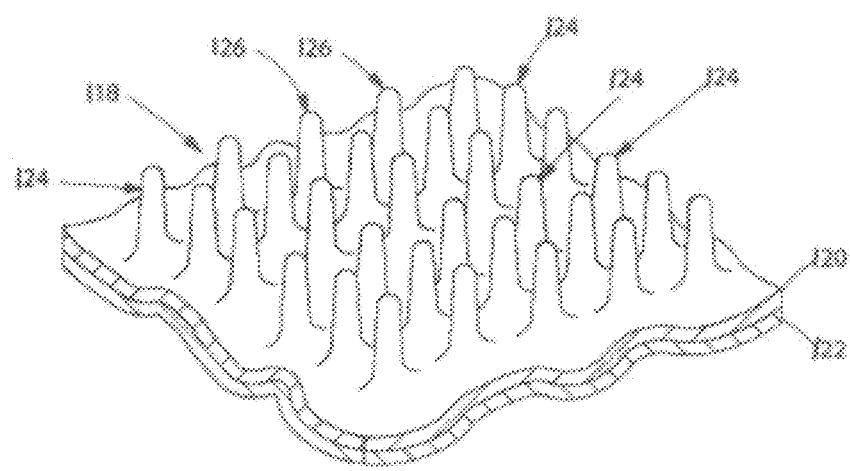
FIG. 4 is a perspective view of a portion of a topsheet of an absorbent article utilized in a method of the present invention.

FIG. 4 shows a preferred topsheet 118 comprising a plurality of discrete extended elements 124. The discrete extended elements 124 are formed as protruded extensions of the web, generally on a first surface thereof. The number, size, and distribution of discrete extended elements 124 on the embossed web 118 can be predetermined based on desired stickiness, soft feel, visual effects, and other consumer-relevant properties. In general, the discrete extended elements 124 protrude only from one surface of embossed web 118, protruding away from the underlying absorbent core and toward the skin of the wearer of the absorbent article. Therefore, when the embossed web 118 is used as a topsheet in a disposable absorbent article, the embossed web 118 can be oriented such that the discrete extended elements 124 are skin contacting for superior softness impression. Furthermore, the distal ends 126 of the extended elements provide a reduced surface area in the plane of the distal ends 126, which can result in a topsheet having reduced stickiness. Moreover, having discrete extended elements 124 with closed distal ends 126 can result in reduced rewet, i.e., reduced amounts of fluid being re-introduced to the surface of the topsheet after having been first passed through apertures of the topsheet to underlying absorbent core (note that apertures, such as macroapertures, are not shown in the Figures herein).

Figure 5:
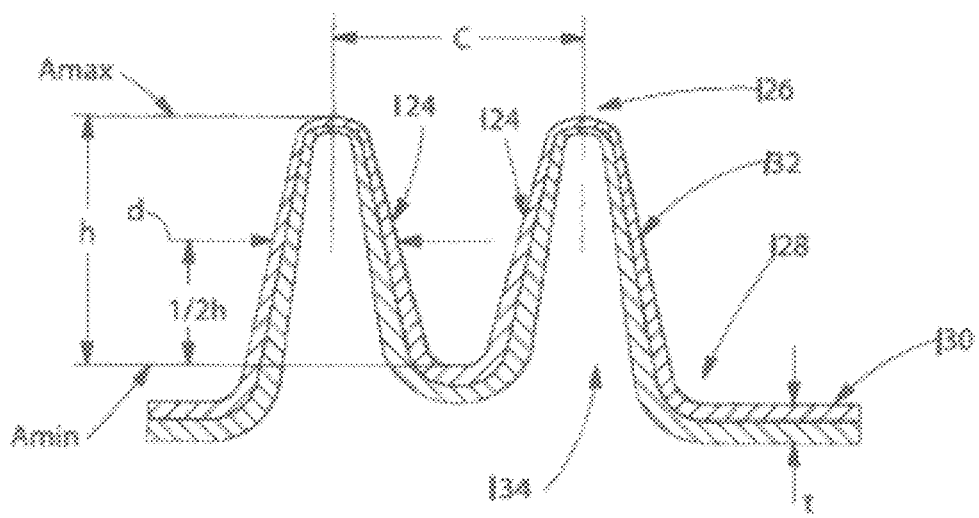
FIG. 5 is a cross-sectional view of a portion of a topsheet of an absorbent article utilized in a method of the present invention.

FIG. 5 is a cross-sectional view of a portion of a preferred topsheet 118. As shown in FIG. 5, discrete extended elements 124 can be described as protruding from first surface 128 of the topsheet 118. As such, the discrete extended elements 124 can be described as being integral with the web of material 130, and formed by permanent local plastic deformation of the web 130. The discrete extended elements 24 can be described as having a side wall(s) 132 defining an open proximal portion 134 and a closed or open distal end 126. The discrete extended elements 124 each have a height h measured from a minimum amplitude $A_{min}$ between adjacent extended elements to a maximum amplitude $A_{max}$ at the closed or open distal end 126. The discrete extended elements have a diameter d, which for a generally cylindrical structure is the outside diameter at a lateral cross-section. By "lateral" is meant generally parallel to the plane of the first surface 28. For generally columnar discrete extended elements having non-uniform lateral cross-sections, and/or non-cylindrical structures of discrete extended elements, diameter d is measured as the average lateral cross-sectional dimension at ½ the height h of the discrete extended element, as shown in FIG. 5. Thus, for each discrete extended element 124, an aspect ratio, defined as h/d, can be determined. The discrete extended element 124 can have an aspect ratio h/d of at least about 0.2, at least about 0.3, at least about 0.5, at least about 0.75, at least about 1, at least about 1.5, at least about 2, at least about 2.5, or at least about 3. The discrete extended elements 124 will typically have a height h of at least about 30 microns, at least about 50 microns, at least about 65, at least about 80 microns, at least about 100 microns, at least about 120 microns, at least about 150 microns, or at least about 200 microns. The extended elements will typically be at least the same height as the thickness of the precursor web, or at least 2 times the thickness of the precursor web, or at least 3 times the thickness of the precursor web. The discrete extended elements 24 will typically have a diameter d of about 50 microns to about 5,000 microns, about 50 microns to about 3,000 microns, about 50 microns to about 500 microns, about 65 microns to about 300 microns, or about 75 microns to about 200 microns. In certain embodiments, the discrete extended elements 24 can have a larger diameter d up to about 2.5 centimeters, up to about 2 centimeters, up to about 1.5 centimeters, up to about 1 cm, up to about 0.5 centimeters, or up to about 0.1 centimeters.

The backsheet is typically impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. In one embodiment, the backsheet can be a breathable backsheet such as that described in U.S. Pat. No. 6,623,464.

Adhesive Substrate

The adhesive substrate utilized in a method of the present invention will typically comprise a substrate and an adhesive material disposed on the substrate.

Suitable substrates for the adhesive substrate include a variety of materials, for example film (e.g. cellophane, acetate, polypropylene, polyester, vinyl, etc.), paper, cloth, mesh, foil, and the like. A preferred substrate is cellophane film or acetate film.

Suitable adhesive materials for the adhesive substrate include pressure sensitive adhesive, acrylic emulsion, acrylic solvent, hot melt rubber, rubber solvent, and the like. A preferred adhesive material is pressure sensitive adhesive.

It will be recognized that the various types of adhesive substrates, as well as the amount of adhesive substrate to be affixed to the outer surface of the absorbent articles, can be selected based on nature of the absorbent articles being tested. Once an appropriate adhesive substrate is selected, the type and amount of adhesive substrate used should remain consistent for the various absorbent articles being tested.

Non-limiting examples of adhesive substrates include pressure sensitive tapes, such as office tape, for example those comprising an acetate or cellophane substrate and a pressure sensitive adhesive (e.g. available under the trade names SCOTCH from 3M, and TESA from Tesa SE). Other examples of adhesive substrates include archival tape, gaffer tape, duct tape, packing tape, masking tape, electrical tape, surgical tape, and the like.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for evaluating the stickiness of an outer surface of an absorbent article, said method comprising the steps of:

providing said absorbent article on a stationary horizontal surface, said outer surface of said absorbent article facing away from said stationary horizontal surface, affixing an adhesive substrate to said outer surface of said absorbent article, grasping an end portion of said adhesive substrate, and lifting said end portion of said adhesive substrate in a direction away from said stationary horizontal surface.

2. The method of claim 1, wherein said adhesive substrate comprises a substrate and an adhesive material disposed on said substrate.

3. The method of claim 2, wherein said substrate of said adhesive substrate is selected from the group consisting of film, paper, cloth, mesh, foil, and combinations thereof.

4. The method of claim 2, wherein said adhesive material of said adhesive substrate is selected from the group consisting of pressure sensitive adhesive, acrylic emulsion, acrylic solvent, hot melt rubber, rubber solvent, and mixtures thereof.

5. The method of claim 1, wherein said adhesive substrate is a pressure sensitive tape.

6. The method of claim 1, wherein said outer surface is a top outer surface of said absorbent article.

7. The method of claim 1, wherein said outer surface of said absorbent article comprises a topsheet material.

8. The method of claim 7, wherein said topsheet material is comprised of a material selected from the group consisting of a thermoplastic film and a nonwoven material.

9. The method of claim 7, wherein said topsheet is a thermoplastic film and comprises a plurality of discrete extended elements.

10. The method of claim 9, wherein said discrete extended elements are generally columnar and have an aspect ratio of at least about 0.2.

11. The method of claim 1, wherein said absorbent article is a first absorbent article and said adhesive substrate is a first adhesive tape, wherein said method further comprises the steps of:

providing a second absorbent article on said stationary horizontal surface, said second absorbent article having an outer surface, wherein said outer surface of said second absorbent article is different from said outer surface of said first absorbent article, affixing a second adhesive tape to said outer surface of said absorbent article, wherein said second adhesive tape has the same composition as said first adhesive tape, grasping an end portion of said second adhesive tape, and lifting said end portion of said second adhesive tape in a direction away from said stationary horizontal surface.

12. The method of claim 11, wherein said method further comprises the step of comparing the degree to which the first adhesive tape detaches from said outer surface of said first absorbent article to the degree to which the second adhesive substrate detaches from said outer surface of said second absorbent article.

13. The method of claim 11, wherein said end portion of said second adhesive tape is lifted at the same time as the end portion of said first adhesive tape is lifted.

14. A method for evaluating the stickiness of an outer surface of an absorbent article, said method comprising the steps of:

providing said absorbent article on a stationary horizontal surface, said outer surface of said absorbent article facing away from said stationary horizontal surface, affixing an adhesive substrate to said outer surface of said absorbent article, grasping an end portion of said adhesive substrate, and lifting said end portion of said adhesive substrate in a direction away from said stationary horizontal surface;

wherein the outer surface of said absorbent article comprises a topsheet material; and wherein said topsheet material is comprised of a material selected from the group consisting of a thermoplastic film.

15. The method of claim 14, wherein said topsheet is a thermoplastic film and comprises a plurality of discrete extended elements.

16. The method of claim 15, wherein said discrete extended elements are generally columnar and have an aspect ratio of at least about 0.2.

17. The method of claim 14, wherein said absorbent article is a first absorbent article and said adhesive substrate is a first adhesive tape, wherein said method further comprises the steps of:

providing a second absorbent article on said stationary horizontal surface, said second absorbent article having an outer surface, wherein said outer surface of said second absorbent article is different from said outer surface of said first absorbent article, affixing a second adhesive tape to said outer surface of said absorbent article, wherein said second adhesive tape has the same composition as said first adhesive tape, grasping an end portion of said second adhesive tape, and lifting said end portion of said second adhesive tape in a direction away from said stationary horizontal surface.

18. The method of claim 17, wherein said method further comprises the step of comparing the degree to which the first adhesive tape detaches from said outer surface of said first absorbent article to the degree to which the second adhesive substrate detaches from said outer surface of said second absorbent article.

19. The method of claim 17, wherein said end portion of said second adhesive tape is lifted at the same time as the end portion of said first adhesive tape is lifted.

* * * * *